United States Patent [19]

Eveland

[11] 4,035,916
[45] July 19, 1977

[54] DENTAL APPARATUS

[76] Inventor: Melborne D. Eveland, 1006 Buena Vista Road, Forked River, N.J. 08731

[21] Appl. No.: 647,412

[22] Filed: Jan. 8, 1976

Related U.S. Application Data

[63] Continuation-in-part of Ser. No. 470,197, May 15, 1974, Pat. No. 3,965,576.

[51] Int. Cl.$^2$ .............................................. A61C 11/00
[52] U.S. Cl. ...................................................... 32/32
[58] Field of Search .............................................. 32/32

[56] References Cited

U.S. PATENT DOCUMENTS

| 1,636,304 | 7/1929 | House | 32/32 |
|---|---|---|---|
| 2,688,800 | 9/1954 | Gerber | 32/32 |
| 3,808,689 | 5/1974 | Spinella | 32/32 |

Primary Examiner—Robert Peshock
Attorney, Agent, or Firm—Robert K. Youtie

[57] ABSTRACT

A dental apparatus wherein dental models are detachably assembled with an articulator in a repeatable relationship by the use of improved dental model attachment members and articulator means affording greater and easier working access to the models and facilitating positioning and manipulation thereof.

19 Claims, 8 Drawing Figures

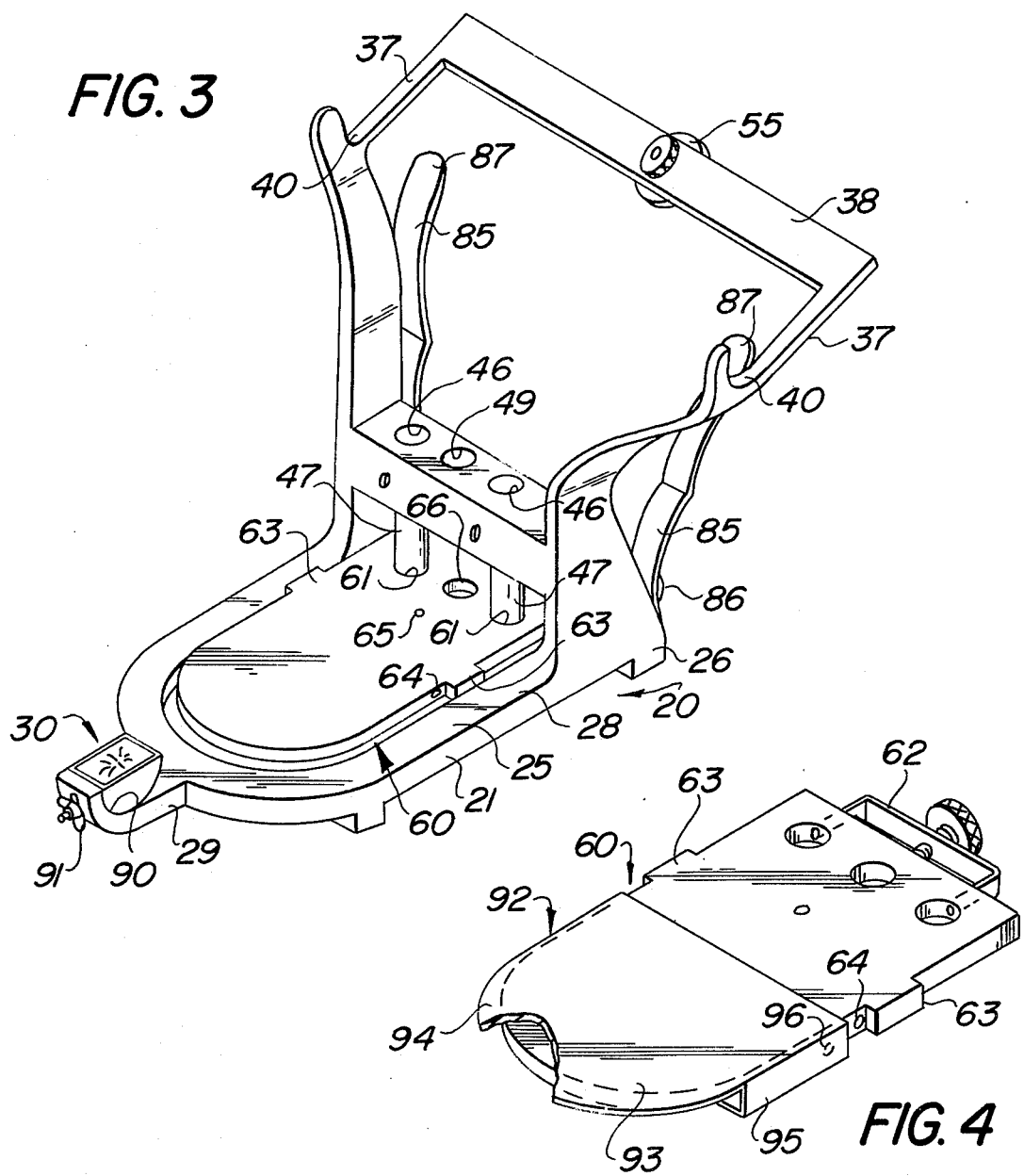

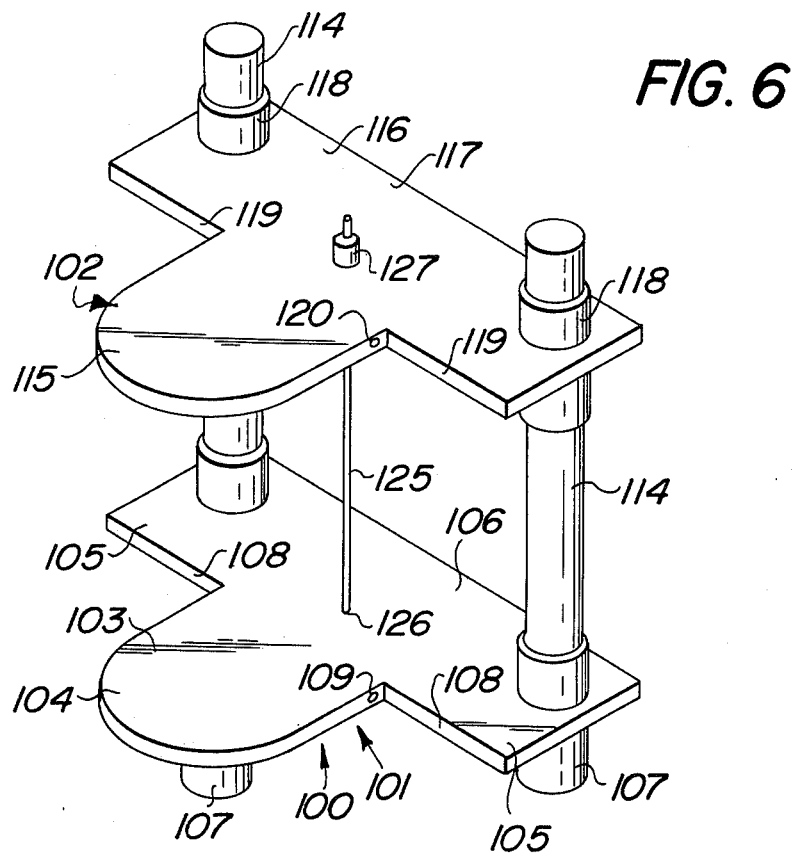
FIG. 6
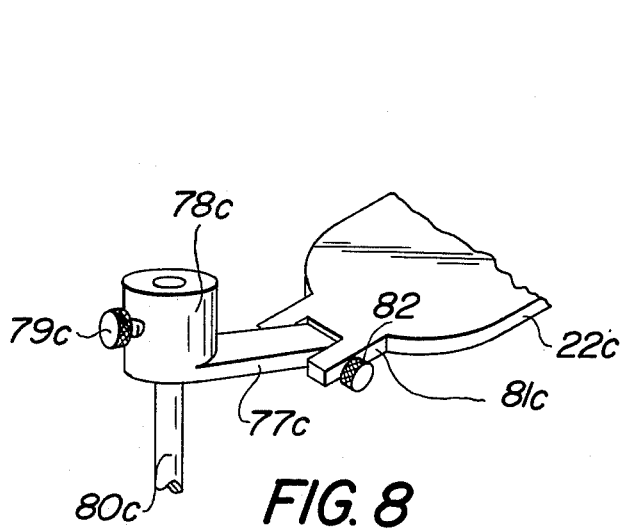
FIG. 7
FIG. 8

DENTAL APPARATUS

CROSS-REFERENCES TO RELATED APPLICATIONS

This application is a continuation-in-part of my co-pending patent application Ser. No. 470,197 filed May 15, 1974 entitled Dental Apparatus and Method and now U.S. Pat. No. 3,965,576 issued June 29, 1976.

BACKGROUND OF THE INVENTION

While the method and apparatus of said copending Patent Application have simplified and speeded certain formerly difficult and time-consuming procedures of dental technicians, the fabrication of dentures, both partial and complete, remains one requiring high skill and experienced judgement.

SUMMARY OF THE INVENTION

It is, therefore, an important object of the present invention to provide apparatus which further simplifies and speeds the fabrication of a wide variety of dentures, and thereby effects substantial savings in costs and time, with concomitant improvements to the resultant product.

It is another object of the present invention to provide dental apparatus of the type described wherein dental models may be removably replaced with respect to the same or different articulators with extreme ease, rapidity, and highly accurate repeatability of relative location.

It is still another object of the present invention to provide dental apparatus having the advantageous characteristics of said copending patent application and those mentioned in the preceding paragraph, and which more particularly includes a unique attachment structure or shim for attaching dental models to an articulator, surveyor, reline jig or other similar mounting member in a simple, expeditious and economical manner.

It is a more particular object of the present invention to provide improvements in a dental articulator affording greater relative adjustability of the dental models to enhance access thereto and facilitate the technician's work.

It is another particular object of the present invention to provide improvements in incisal guide cups to simplify use thereof and increase the range of adjustability and versatility.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 3 is a view similar to FIG. 1, but with the top articulator member and its mount removed.

FIG. 4 is a perspective view showing an articulator member apart from the articulator and including an attachment member or shim in an intermediate position of replacement on the attachment member.

FIG. 5 is a perspective view showing a slightly modified attachment member or shim of the present invention.

FIG. 6 is a top, front perspective view showing a work positioning apparatus or jig of the present invention.

FIG. 7 is a perspective view showing an incisal guide member apart from an articulator.

FIG. 8 is a partial perspective view showing a slightly modified embodiment of incisal guide pin arm of the present invention.

DESCRIPTION OF THE PREFERRED EMBODIMENTS

Figure 1:
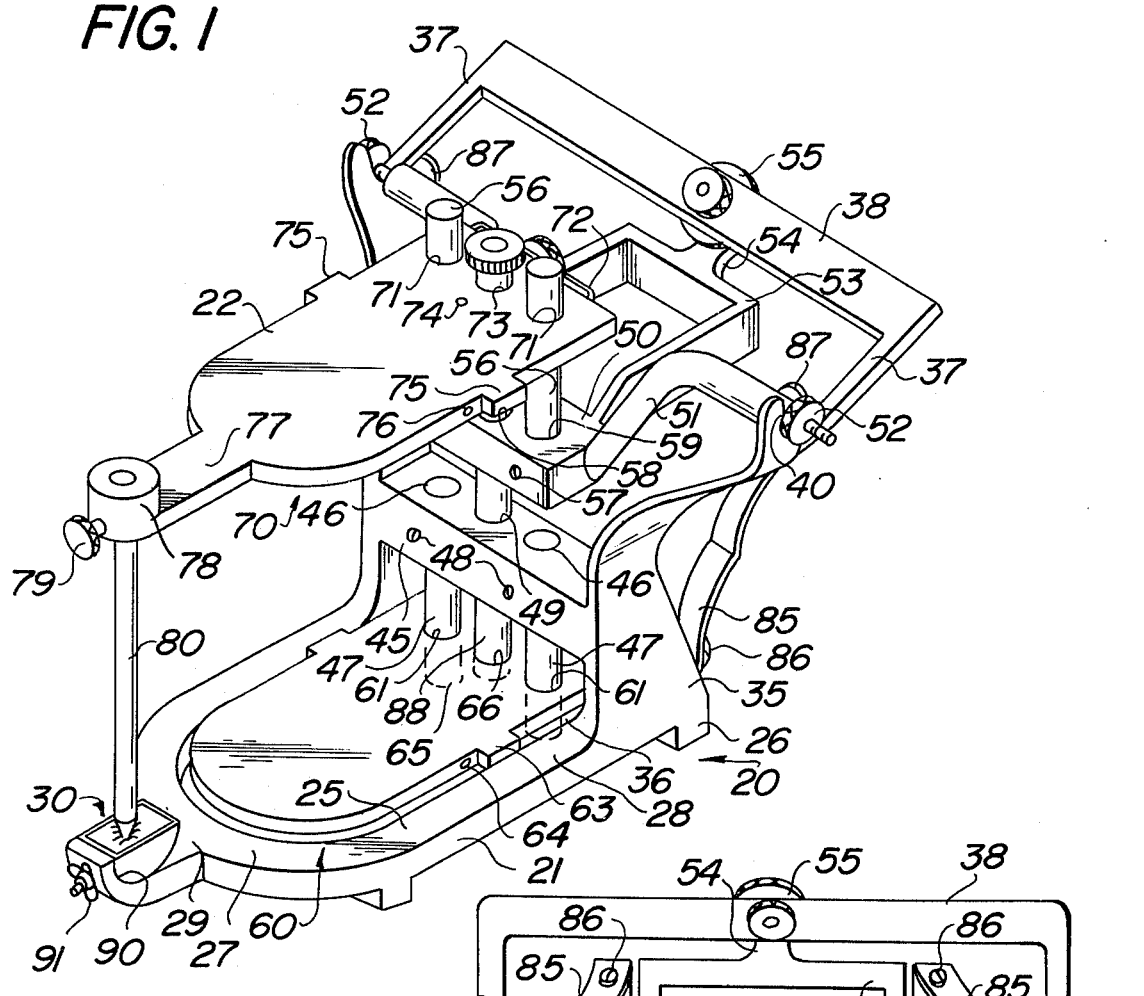
FIG. 1 is a top, front perspective view showing an articulator constructed in accordance with the present invention.
Figure 2:
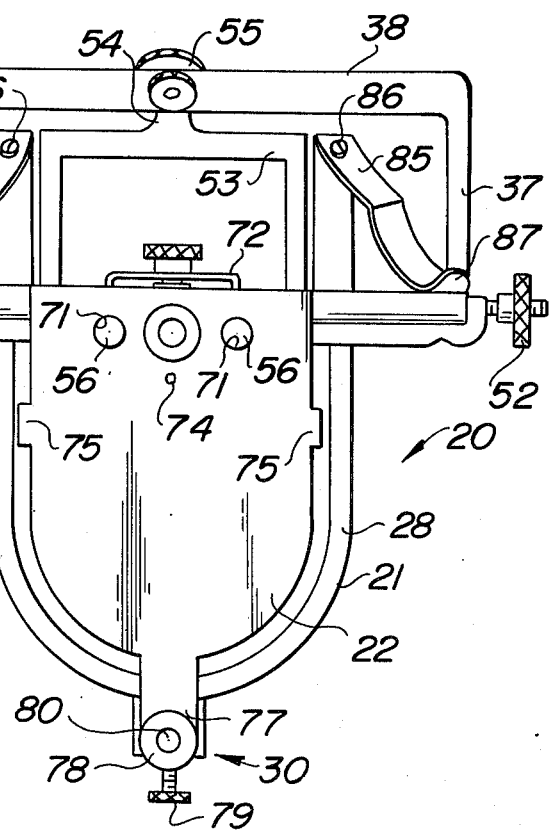
FIG. 2 is a top view of the articulator of FIG. 1.

Referring now more particularly to the drawings, and specifically to FIGS. 1–3 thereof, an articulator of the present invention is there generally designated 20 and includes a base or stand 21 adapted to rest on a support, and an upper part 22, carried for rotation about an elevated generally horizontal axis. The articulator base 21 may include a generally horizontal open frame 25 normally disposed substantially horizontally and having at spaced locations thereabout depending feet 26 for supporting engagement with a nether surface. The base frame 25 may be generally U-shaped, as illustrated, including a forward bight portion 27 and side legs 28 extending from opposite ends of the bight portion. Extending forwardly from a medial region of the bight portion 27 may be an arm, projection or lug 29 for carrying an incisal guide, generally designated 30.

Upstanding from the rear end of each side 28 may be an upstanding member, side wall or pedestal element 35. Thus, the upstanding members or side walls 35 combine to define pedestal means having a medially open region 36, as between the laterally spaced uprights. The upper regions of pedestal elements 35 are formed to extend obliquely, as at 37, being provided at their upper ends with a laterally extending crosspiece or bridging member 38. The oblique upper pedestal regions 37 are each provided with open journal bearings, as at 40, in generally horizontal, laterally extending alignment with each other.

A lower member mounting bar 45 extends in fixed relation laterally across the space 36 between intermediate regions of pedestal elements 35, spaced above the base 21. Thus, the mounting member or bar 45 bridges the pedestal opening 36. The lower member mounting bar 45 may have a pair of laterally spaced, generally parallel, substantially vertical through holes 46. The holes 46 are for slidably receiving respective way members or pins 47, the latter being selectively adjustable vertically and releasably retained in a selected position by suitable retention means, such as set screws 48. An additional generally vertical through hole 49 is provided in the lower member mounting bar 45, for a purpose appearing presently.

Above the lower member mounting bar 45 is an upper member mounting bar 50, extending generally horizontally and laterally between respective pedestals 35. The upper member mounting bar 50 may be provided at opposite ends with respective rearward extensions 51 each having its distal end portion extending laterally outwardly, as at 52 and there defining a shaft rotatably received in the adjacent journal bearing 40. The rotative shafts 52 of the arms 51 are in generally laterally extending, horizontal alignment with each other. By this means, the upper member mount 50 is rotatable about the aligned axes of shafts 52 toward and away from the lower member mount 45. A generally U-shaped rearward extension 53 is provided on the back of upper member mount 50 and includes an extension or finger 54 extending rearwardly generally beneath the fixed bridge 38. There may be carried by the bridge an adjustable stop member 55, say a headed member threadedly engaged through the bridge 38 for selective vertical adjustment relative to the latter. The stop member 55 is thus engageable with the finger 54 to limit downward swinging movement of mounting member 50 to selected position.

The upper member mounting bar 50 is provided with a pair of generally parallel through holes 59 similar to the holes 46 of the lower member mounting bar 45. A pair of upper ways or rods 56 are respectively slidably engaged in holes 59 and there retained in suitable position by holding means 57, such as set screws, or the like. An additional through hole 58 is provided in the upper member mounting bar 50 for alignment with the through hole 49 of lower mounting bar 45, in a manner presently appearing more fully.

A generally plate-like lower member 60 is shaped for conformable reception within the U-shaped base structure 25 and is formed with a pair of laterally spaced through holes or openings 61 respectively receiving way means or rods 47. That is, the lower member or plate 60 is generally horizontal and slidable vertically on the way means or rods 47 to a selected elevation, at which the mounting member may be secured by suitable holding means 62, which may include the set screws, or the equivalent carried by the mounting member and in releasable holding engagement with the rods 47.

An additional through opening or hole 66 may be provided through the lower mounting member 60 in alignment with the hole 49 of mounting member 45, for a purpose appearing presently. Also, the lower member may be provided with abutments or stop elements on opposite side edges, such as outstanding ears or lugs 63, and a suitable detent element 64, such as a spring pressed ball. In addition, the upper surface of the lower member plate may be provided with a recess 65 for a bight pin, as will appear hereinafter.

A generally plate-like upper member, similar to lower member 60, is generally designated 70, and is illustrated in FIG. 1 as spaced over the lower member. The upper member similarly has a pair of spaced through holes 71 receiving respective way members or rods 56 and provided with suitable holding means 72, say in the nature of set screws or the like carried by the upper member and releasably abuttingly engageable with the rods 56. The upper member 70 is further provided with a through opening or hole 73 located for alignment with the hole 58 of upper mounting member 50. Also provided in upper member 70 is a bight pin receiver or hole 74 for a purpose appearing presently.

Similar to the lower member 60, the upper member is provided with stop means, abutments or lugs 75, say on opposite side edges of the upper member, and may be further provided with holding means, such as spring pressed balls 76 also on opposite side edges.

In addition, the upper member 70 may be provided with a forward end extension 77 including an open ended cylindrical receiver 78, as for receiving a follower pin 80, and may be provided with locking means 79, in the form of a set screw.

The upper part 22 may thus be considered as composed of the upper member 70, way means 56, upper mounting member 50, together with its rearward extensions 51 and bearing shafts 52. Adjacent to the rearward side of each pedestal or side wall 35, there is provided a suitable resilient urging means, such as a leaf spring 85 having its lower end suitably secured, as by fasteners 86 to the base 21, and having its upper region 87 resiliently bearing against the rearward extension 51 to urge the upper part 22 in its forward and downward direction of rotation about the aligned axes of the shafts 52. Thus, there are a pair of resilient members or leaf springs 85, best seen in FIGS. 2 and 3, laterally spaced apart so as to leave the rearward side of the articulator relatively open for convenient working access therethrough.

In order to align the lower and upper members 60 and 70, say in accurate parallelism with each other, a paralleling rod or alignment pin 88 may be removably extended through the several holes 73 of upper members 70, 58 of upper mounting member 50, 49 of lower mounting member 45 and 66 of lower member 60. The adjustable stop 55 may then be set to engage abutment finger 54 and the alignment member 88 removed, whereupon the upper part 22 is swingable about the axes of shafts 52 and returnable by the urgence of resilient means 85 to the parallel relation of upper member 70 with lower member 60.

In addition, the forward extension 29 on base 21 may include a generally semicircular upwardly facing formation or groove 90 conformably receiving the incisal guide cup 30 which has an arcuate undersurface so as to be mounted for rotative adjustment. The arcuate formation or groove 90 may be of an angular extent slightly greater than semicircular for retaining the incisal guide cup against upward withdrawal, while permitting lateral withdrawal, if desired. Further, suitable holding means 91, such as a set screw, may be threadedly engaged through guide cup holding extension 29 to releasably retain the guide cup in any selected position of its angular adjustment.

Referring now to FIG. 4, there is seen a lower member 60 apart from the articulator 20. In addition, there is shown an attachment member or shim 92 in an intermediate position of application to or removal from the lower member. The attachment member or shim 92 may include a generally flat plate 93 having its upper or outer side 94 adapted to carry a dental model suitably affixed thereto. The underside of plate 93 is adapted for facing engagement with the upper surface of lower member 60.

Additionally, the plate 93 of attachment member 92 is provided along opposite side edges with inturned clips or channels 95 adapted to slidably receive respective adjacent side edge portions of the lower member 60. That is, the clips 95 define open ended receivers for sliding embracing engagement with adjacent side edge portions of the lower member. By this means, the attachment member 93 is slidable onto and withdrawable from the lower member 60. For accurate and repeatable positioning, the attachment member 92 is slidable onto the lower member 60 into abutting, limiting engagement with the ears or stops 63. At this location, the spring biased detent or ball 64 is snap engageable into a dimple or recess 96 formed in each clip 95. The attachment member 92, and a dental model carried thereby, are effectively retained in a predetermined position on the lower member 60 by the holding means defined of abutments 63 and detent 64, 96, while being removable upon deliberate withdrawal of the attachment member sufficient to depress the balls 64.

While a dental model may be secured to the plate 93 of attachment member 92 by suitable adhesive means, it may be desirable to afford a positive securement. Toward this end, there is shown in FIG. 5 a slightly modified attachment member 92a having a plate 93a and open-ended side clips 95a, all essentially similar to those described in connection with attachment member 92. However, on the upper or outer surface 94a of plate 93a there may be provided, suitably fixed thereto, an undercut formation 98, to which plaster may be positively attached. While the undercut formation 98 assumes an elongate, arcuate formation of T-shaped cross-section, it is appreciated that other undercut formations may be employed, such as headed lugs, or the like.

Referring now to FIG. 6, there is shown therein a jig generally designated 100 which may be used in practice of the instant invention to properly locate dental models on attachment members. The jig includes lower and upper members, respectively designated 101 and 102. The lower member includes a generally horizontal lower plate or base 103 having a working portion 104 generally conforming in size and shape to the lower member 60 of the articulator, and provided at its rearward end with a pair of laterally outstanding, generally coplanar extensions 105. That is, the laterally outstanding extensions 105 combine with the rearward region of the lower member 103 to define a cross-portion 106. The lower member 103 may be mounted on depending feet 107 as at the forward end of working portion 104 and the outer ends of cross-portion 106. The forward edges 108 of the lateral projections 105 are in alignment with each other on opposite sides of the working portion 104, outstanding from opposite side edges thereof and correspond to the forward edges of abutment ears 63, as will appear presently. Additionally, the side edges of the working portion 104 of lower member 103, adjacent to the abutment edges 108, are preferably provided with detent means 109, say springed pressed balls, similar to the detent means 64 of the lower member 60.

Upstanding from the base part 101, at opposite lateral extensions 105, are rods or posts 114, and the upper member 102 is mounted on the posts 114 for up-and-down sliding movement away from and toward the lower member 101. The upper member 102 is similar to the lower member 101, including a working part 115 corresponding in size and shape to the upper member 70 of the articulator and spaced over the working part 103 of the lower member 101. In addition, a pair of generally coplanar lateral extensions 116 are provided on the rearward region of the working part 115 combining to define therewith a rearward cross-part 117 spaced over the rearward cross-part 106 of the base 101. The lateral extensions 116 are provided with through openings, sleeves or bushings 118 respectively slidably receiving the posts 114 and thereby mounting the upper member 102 generally horizontally in spaced parallelism over the lower member 101 for movement vertically toward and away from the latter. The forward edges 119 of the lateral extensions 116 define limits or abutments for a shim or attachment member engaged on the working portion 115, and there may be provided detents 120, such as spring pressed balls, for releasably holding an attachment member in predetermined position on the upper member 102.

In operation, a pair of upper and lower attachment members or shim plates are applied in the predetermined positions on the upper and lower members 102 and 101 of the jig 100. A dental model assembly of upper and lower dental models suitably secured together, is interposed between the attachment members and suitably secured thereto, as by adhesive, plaster, or other. A removable bight pin 125 is inserted through a hole in the upper cross-part 117 to engage in an aligned recess 126 in the lower cross-part 106. A sleeve 127 may then be crimped on the upwardly projecting portion of the pin 125 so as to rest on the upper side of cross-part 117 when the pin 125 rests in the recess 126. This bight pin is then retained with the dental models so that proper spacing thereof can be repeated after the models are separated from each other.

The secured models and attachment members may then be transferred to the articulator, the lower and upper members 60 and 70 being properly adjusted and spaced to receive lower and upper attachment members. Upon separation of the dental models, the lower and upper members may be moved, as desired, by the technician. A later repositioning in centric position may be obtained by inserting the bight pin 125 associated with the particular dental models through the holes 74 of the upper articulator member 70 until the sleeve or shoulder 127 rests on the upper member and the lower end of the bight pin rests in the recess 65 of the articulator lower member 60.

In use of the incisal cup 30, an incisal pin 80 may be inserted downwardly through sleeve 78, locked therein at a suitable position, and its lower end moved to follow along the contour of the cup 30. Of course, incisal cups 30 may be of different internal configurations, say having internal cusp-shaped configurations of different angles, as desired. Also, the orientation of the incisal cup may be selected by rotation and locking at a desired position by means of locking member 91. A modified embodiment of incisal cup is shown in FIG. 7 and there generally designated 30b, including an internal cusp-shaped configuration bounded along its side and rear borders by a raised edge or lip 130 which facilitates the operation by retaining the lower end of the pin within the cup.

A further embodiment of incisal guide pin receiver is shown in FIG. 8, having a suitable arm 77c carrying at its outer end a tube or receiver 78c and pivotally connected at its inner end to an extension 81c of the upper part 22c. The pivotal connection between the arm 77c and the extension 81c may be by means of a pintle 82 adapted to lock the arms 77c in a selected position of its swinging movement. Also, additional locking means 79c may be provided as a set screw on the tubular receiver 78c to removably retain a guide pin 80c inserted through and depending from the receiver. This affords angular adjustment to the incisal guide pin, as for accommodating to the position of the upper part 22c.

From the foregoing, it is seen that the present invention provides dental apparatus which substantially improves the procedures required in manufacture of dentures, effecting considerable reduction in time and costs to all concerned, while enhancing accuracy and appearance of the resultant dentures, and otherwise fully accomplishing their intended objects.

Although the present invention has been described in some detail by way of illustration and example for purposes of clarity of understanding, it is understood that certain changes and modifications may be made within the spirit of the invention.

What is claimed is:

1. A dental articulator comprising a base adapted to rest on a supporting surface, upstanding medially open pedestal means on said base, a lower member in upwardly facing relation on said base for detachably carrying a lower dental model, lower member mounting means on a vertically intermediate region of said pedestal mounting said lower member for vertical adjustment relative to said base, journal bearing means at an upper region of said pedestal, an upper member extending generally from an upper region of said pedestal in downwardly facing relation over said lower member for detachably carrying an upper dental model, upper member mounting means rotatably carried by said bearing means for rotation about a laterally extending generally horizontal axis and mounting said upper member for adjustment transverse of said axis toward and away from said lower member and rotative movement with said upper member mounting means, and spring means on at least one side of said pedestal and operatively connected to said upper member mounting means for urging the latter about its axis for swinging movement of said upper member toward said lower member, said spring means leaving the medial pedestal region open for access therethrough to the dental models, said lower member mounting means comprising a fixed laterally extending member in the medial opening of said pedestal, lower way means depending from said fixed laterally extending member and slidably received in said lower member, and lower member holding means for selectively holding said lower member relative to said lower way means at a desired elevation.

2. A dental articulator according to claim 1, said spring means comprising at least one leaf spring fixed at one end relative to said base and having its other end in resilient bearing engagement with said upper member mounting means.

3. A dental articulator according to claim 1, said upper member mounting means comprising a movable laterally extending member above said fixed laterally extending member and swingable about said axis between a lower position toward and an upper position away from said fixed laterally extending member, upper way means upstanding from said movable laterally extending member and slidably received in said upper member, and upper member holding means for selectively holding said upper member relative to said upper way means at a selected elevation.

4. A dental articulator according to claim 1, in combination with alignment means extending removably through said lower and upper member mounting means to align said upper and lower members in a predetermined relation.

5. A dental articulator according to claim 3, in combination with alignment means extending removably through said lower and upper members to achieve a predetermined alignment.

6. A dental articulator comprising a base adapted to rest on a supporting surface, upstanding medially open pedestal means on said base, a lower member in upwardly facing relation on said base for detachably carrying a lower dental model, lower member mounting means on a vertically intermediate region of said pedestal mounting said lower member for vertical adjustment relative to said base, journal bearing means at an upper region of said pedestal, an upper member extending generally from an upper region of said pedestal in downwardly facing relation over said lower member for detachably carrying an upper dental model, upper member mounting means rotatably carried by said bearing means for rotation about a laterally extending generally horizontal axis and mounting said upper member for adjustment transverse of said axis toward and away from said lower member and rotative movement with said upper member mounting means, spring means on at least one side of said pedestal and operatively connected to said upper member mounting means for urging the latter about its axis for swinging movement of said upper member toward said lower member, said spring means leaving the medial pedestal region open for access therethrough to the dental models, vertical bight pin receiver means in said lower and upper members, and a vertical bight pin removably engageable in said receiver means for repetitive location of said lower and upper members.

7. A dental articulator comprising a base adapted to rest on a supporting surface, upstanding medially open pedestal means on said base, a lower member in upwardly facing relation on said base for detachably carrying a lower dental model, lower member mounting means on a vertically intermediate region of said pedestal mounting said lower member for vertical adjustment relative to said base, journal bearing means at an upper region of said pedestal, an upper member extending generally from an upper region of said pedestal in downwardly facing relation over said lower member for detachably carrying an upper dental model, upper mounting means rotatably carried by said bearing means for rotation about a laterally extending generally horizontal axis and mounting said upper member for adjustment transverse of said axis toward and away from said lower member and rotation about said axis toward and away from said lower member, spring means on said pedestal and operatively connected to said upper member mounting means for urging the latter about its axis for swinging said upper member toward said lower member, and attachment members for fixed securement to said upper and lower dental models and releasable securement to respective upper and lower members, said attachment members each comprising a carrying plate for carrying a dental model on one side and facing relation with a mounting member on the other side, generally parallelly opposed clips on each carrying plate for sliding engagement about and receiving opposite edges of the associated mounting member, and holding means on each mounting member for locating the carrying plate relative to the mounting member.

8. A dental articulator according to claim 7, said clips being open for endwise sliding engagement of said carrier plate and clips with respect to the associated mounting member.

9. A dental articulator according to claim 8, said holding means comprising an abutment for limiting engagement with the leading edge upon said sliding engagement.

10. A dental articulator according to claim 8, in combination with undercut formations on said one side of said carrier plate for retaining engagement with a dental model.

11. An attachment member for attaching a dental model to an articulator, surveyor, reline jig or other mounting member, said attachment member comprising a carrying plate for carrying a dental model on one side and facing engagement with a mounting member on the other side, generally parallelly opposed clips on the carrier plate for slidably receiving opposite edges of the associated mounting member, and holding means for engagement with the mounting member to locate the carrier plate relative to the mounting member.

12. An attachment member according to claim 11, said clips being open for endwise sliding engagement of the carrier plate and clips with respect to an associated mounting member.

13. An attachment member according to claim 12, said holding means comprising an abutment surface for limiting engagement with a mounting member.

14. An attachment member according to claim 12, in combination with an undercut formation on said one side of said carrying plate for retaining engagement with a dental model.

15. A dental articulator comprising a base adapted to rest on a supporting surface upstanding medially open pedestal means on said base, a lower member in upwardly facing relation on said base for detachably carrying a lower dental model, lower member mounting means on a vertically intermediate region of said pedestal mounting said lower member for vertical adjustment relative to said base, journal bearing means at an upper region of said pedestal, an upper member extending generally from an upper region of said pedestal in downwardly facing relation over said lower member for detachably carrying an upper dental model, upper member mounting means rotatably carried by said bearing means for rotation about a laterally extending generally horizontal axis and mounting said upper member for adjustment transverse of said axis toward and away from said lower member and rotation about said axis toward and away from said lower member, spring means on said pedestal and operatively connected to said upper member mounting means for urging the latter about its axis for swinging said upper member toward said lower member, and an internally cusp-shaped guide member facing upwardly from said base, guide member mounting means on said base for mounting said guide member at a selected angle of orientation, and a follower depending from said upper member for following engagement with said guide member.

16. A dental articulator according to claim 15, said guide member mounting means comprising a receiver rotatably receiving said guide member.

17. A dental articulator according to claim 15, said guide member mounting means comprising a guide member receiver mounted for selective rotation relative to said base.

18. A dental articulator according to claim 15, in combination with a retaining flange about said guide member for retaining engagement with said follower.

19. A dental articulator according to claim 15, in combination with means mounting said follower for angular adjustment relative to said upper member.

* * * * *